United States Patent [19]
Arlinghaus et al.

[11] Patent Number: 5,821,060
[45] Date of Patent: Oct. 13, 1998

[54] DNA SEQUENCING, MAPPING, AND DIAGNOSTIC PROCESSES USING HYBRIDIZATION CHIPS AND UNLABELED DNA

[75] Inventors: Heinrich F. Arlinghaus; K. Bruce Jacobson, both of Oak Ridge, Tenn.

[73] Assignee: Atom Sciences, Inc., Oak Ridge, Tenn.

[21] Appl. No.: 691,614

[22] Filed: Aug. 2, 1996

[51] Int. Cl.[6] ............................ C12Q 1/68; G01N 33/48; B01D 59/44
[52] U.S. Cl. ........................... 435/6; 435/7.1; 435/287.2; 435/288.7; 436/173; 530/300; 536/24.3; 250/282; 250/423 P
[58] Field of Search ............................ 435/6, 7.1, 287.2, 435/288.7; 536/24.3; 530/300; 436/173; 250/282, 423 P

[56] References Cited

U.S. PATENT DOCUMENTS

| | | | |
|---|---|---|---|
| 5,202,231 | 4/1993 | Drmanac et al. | 435/6 |
| 5,539,082 | 7/1996 | Nielsen et al. | 530/300 |
| 5,547,835 | 8/1996 | Koster et al. | 435/6 |
| 5,580,733 | 12/1996 | Levis et al. | 435/6 |

FOREIGN PATENT DOCUMENTS 8910977  11/1989  WIPO .

OTHER PUBLICATIONS

Peter E. Nielsen, Michael Egholm, Rolf H. Berg, and Ole Buchardt, "Sequence–Selective Recognition of DNA by Strand Displacement with a Thymine–Substituted Polyamide", *Science* 254, pp. 1496–1500, (Dec. 1991).

Michael Egholm, Ole Buchardt, Leif Christensen, Carsten Behrens, Susan M. Freier, David A. Driver, Rolf H. Berg, Seog K. Kim, Bengt Norden & Peter E. Nielsen, "PNA Hybridizes to Complementary Oligonucleotides Obeying the Watson–Crick Hydrogen–Bonding Rules", *Nature* 365, pp. 566–568, (Oct. 1993).

Wittung et al., Nucleic Acids Research 22(24):5371–5377 1994.

Wittung et al., Nature 368:561–563 Apr. 1994.

*Primary Examiner*—W. Gary Jones
*Assistant Examiner*—Paul B. Tran
*Attorney, Agent, or Firm*—Pitts & Brittian, P.C.

[57] ABSTRACT

A process for deoxyribonucleic acid (DNA) sequencing, mapping, and diagnostics which utilizes the differences between the chemical composition of DNA and that of peptide nucleic acids (PNAs) to provide DNA sequencing, mapping, or diagnostics using natural DNA fragments, rather than using radioisotopes, stable isotopes or fluorescent substances to label the DNAs. The process includes the steps of hybridizing PNA segments to complementary DNA segments which are fixed to a hybridization surface, or hybridizing DNA segments to complementary PNA segments which are fixed to a hybridization surface, and using mass spectrometric or non-mass spectrometric techniques to analyze the extent of hybridization at each potential hybridization site.

42 Claims, 1 Drawing Sheet

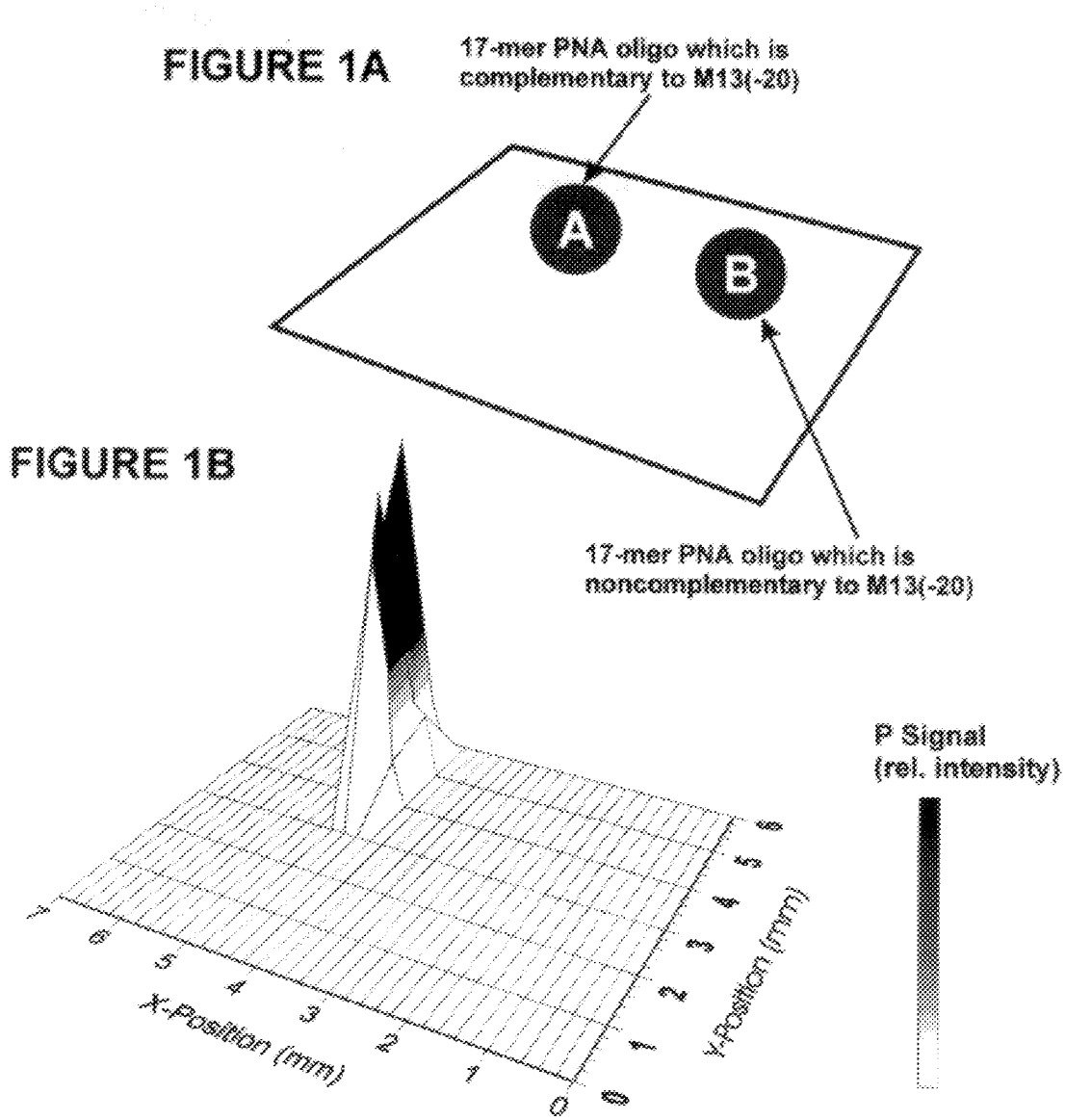

DNA SEQUENCING, MAPPING, AND DIAGNOSTIC PROCESSES USING HYBRIDIZATION CHIPS AND UNLABELED DNA

TECHNICAL FIELD

This invention is related to the fields of deoxyribonucleic acid (DNA) sequencing, mapping, and diagnostics. More particularly this invention takes advantage of the differences between the chemical composition of DNA and that of peptide nucleic acids (PNAs) to provide DNA sequencing, mapping, or diagnostics using natural DNA fragments, rather than using radioisotopes, stable isotopes or fluorescent substances to label the DNAs.

BACKGROUND ART

The nuclei of living cells possess chromosomes which contain the genetic information necessary for the growth, regeneration and other functioning of organisms. Instructions concerning such functioning are contained in the molecules of deoxyribonucleic acid (DNA). DNA is contained within the chromosome in a form of complimentary strands commonly thought of as being configured in a double helix.

Genetic information in DNA is known to be contained within the sequence of nucleotide bases which are arranged on a linear polymer of deoxyribose phosphate. The four bases consist of thymine (T), adenine (A), cytosine (C), and guanine (G). The two strands of the DNA double helix are joined in accordance with well known base pairing rules. These rules provide that T joins with A and that C joins with G. Accordingly, the base sequence along one strand determines the order of bases along the complementary strand.

Genetic and diagnostic information can be gathered by determining the sequence of bases in DNA strands. Heretofore, DNA sequencing has been accomplished by obtaining DNA from a source of interest and segregating a template DNA fragment. A complementary DNA fragment is synthesized by binding a primer ODN to the template fragment. This template fragment with the primer attached is then introduced into a solution containing deoxyribonucleoside triphosphates, DNA polymerase, buffer and magnesium ions.

The polymerase chain reaction, or PCR, is a process which utilizes a heat stable form of the DNA polymerase to extend the primer and transcribe the DNA template. The combination of template and primers is employed to limit the size of the DNA produced. This size can vary from a few dozen to several hundred or several thousand nucleotides in the DNA product. During the synthesis of this DNA product, certain labels are incorporated into the primer and/or the incoming nucleotides so that the product can be identified. The region of the genomic DNA that is transcribed is determined by the sequence of the primers employed. One primer is used in one strand of DNA and another is used for the complementary strand. The distance between the binding sites of the two primers determines the length of the DNA product. In one cycle of the polymerase chain reaction, the primer binds to the template DNA, the polymerase transcribes the template DNA beginning at the primer's 3' terminus and DNA products are released from the template. These events occur at different temperatures. Template binding occurs between 35°–50° C., polymerase activity between 60°–75° C., and the release between 85°–97° C. This cycle is repeated until sufficient DNA product is made to perform an analysis.

Recent advances in molecular biology and the schedule in the Human Genome Project have spurred the development of new methods for the labeling and detection of DNA and DNA fragments. Traditionally, radioisotopes have served as sensitive labels for DNA while, more recently, fluorescent, chemiluminescent and bioactive reporter groups have also been utilized. Fluorescent and chemiluminescent labels function by the emission of light as a result of the absorption of radiation and chemical reactions, respectively. Bioactive labels employ substances derived from living tissue.

The reporter group, $^{32}P$ or certain fluorescent or chemiluminescent substances, are usually incorporated in the primers or the deoxynucleoside triphosphates to label the newly synthesized DNA fragments. In the normal application, the DNA fragments or ODNs are allowed to hybridize respectively to a set of bound ODNs or DNA fragments that are immobilized on a solid surface. Because hybridization generally involves the formation of hydrogen bonds between adenines and thymines and between guanines and cytosines in opposing DNA strands, the stable binding of one DNA to another through such hydrogen bonds reveals the sequence in the DNA fragments if the sequences of the immobilized ODNs are known. This process is sometimes referred to as "sequencing by hybridization" (SBH). The DNA on the solid surface is sometimes referred to as an "SBH chip" or a genosensor chip or a hybridization surface. This version of the SBH process is referred to as Format II SBH. E. Southern disclosed Format II SBH in International Application No. PCT/GB89/00460. Affymetrix, Inc. is very active in developing commercial products to perform Format II SBH.

Format I SBH is an alternative method where the genomic DNA is attached to a solid surface, such as a nylon membrane, and the ODNs of known sequence and containing labels are allowed to hybridize. R. Drmanac and R. Czerkvenjakov disclosed Format I SBH in U.S. Pat. No. 5,202,231, and are developing the analyses commercially at Hyseq Co.

While the above sequencing technique is capable of producing reliable results if properly applied, certain disadvantages are inherent in the process. For example, the ability to resolve adjacent $^{32}P$ labels is limited by the length of the beta particle track produced by the disintegration of $^{32}P$. With fluorescent labels, the most common labels in use today, fluorescence from the solid surface of the SBH chip itself interferes with the detection of the signal from the fluorescent label on the DNA. It is common to see a signal to noise ratio of only 3:1 for fluorescent labels.

The peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, *Science* 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, *Nature* 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

Accordingly, it is an object of the present invention to provide a DNA sequencing, mapping, or diagnostic process in which normal, unlabeled DNA is used, rather than DNA labeled with stable isotopes, radioactive isotopes, fluorescent groups, or any other molecular species attached to DNA for the purpose of identification. This will eliminate the reagents and labor involved in labeling the DNA and therefore significantly reduce the analysis costs.

A further object of this invention is the use of PNA fragments of known sequence to be used in place of DNA fragments (ODNs) in Type II SBH. In this case, the presence of DNA hybridization at a particular PNA sequence location would be determined by detecting unique components of DNA, such as phosphorus, phosphorus oxide, or deoxyribose derivatives. The efficiency of detection of phosphorus and/or phosphorus compounds derived from the DNA should enable detection of $10^{-15}$ to $10^{-18}$ moles of phosphorus or its compounds and allow detection of $10^{10}$ to $10^{12}$ molecules of DNA on a given site.

Another object of this invention is the use of PNA fragments of known sequence in place of ODNs in Type I SBH. For this application, PNA which is hybridized to the DNA would cover the unique components of DNA, such as phosphorus or deoxyribose derivatives and a surface detection method would see an absence of these materials at the hybridization location(s).

Yet another object of the present invention is to use mass spectrometric techniques for measurement of unique components of DNA, such as phosphorus, phosphorus oxides, or deoxyribose derivatives, that are not components of PNAs.

Still another object of the present invention is to provide surface detection methods, including but not limited to Raman spectroscopy, surface-enhanced Raman spectroscopy, second-harmonic generation on surfaces, polarization techniques such as ellipsometry, and laser-induced emission, which can readily identify the difference between DNA and PNA on hybridized surfaces.

Other objects and advantages over the prior art will become apparent to those skilled in the art upon reading the detailed descriptions as follows.

DISCLOSURE OF THE INVENTION

In accordance with various features of the present invention, a DNA sequencing, mapping, and diagnostic process using unlabeled DNA is provided. In Format II SBH, the DNA fragments are obtained by fragmentation procedures, and hybridized to a set of PNAs of known sequences that are fixed on a solid surface. In Format I SBH, the DNA fragments are localized on the genosensor chip and the PNAs of known sequence would be hybridized to the DNAs. The sequence in the unknown DNA is known from the sequences of the test PNAs to which it hybridized. The occurrence of hybridization-is determined by detection of the presence (Format II) or absence (Format I) of unique components of DNA, such as phosphorus, phosphorus oxides, or deoxyribose derivatives, at the surface of the genosensor chip. Detection methods include mass spectrometric techniques and resonance ionization spectroscopy (RIS). RIS can be used to probe a spatially resolved portion of a surface by combining it with ion sputtering (Sputter-Initiated Resonance Ionization Spectroscopy, SIRIS) or laser ablation (Laser Ablation Resonance Ionization Spectroscopy, LARIS).

Format II SBH requires that the PNA be attached to a genosensor surface. The surface to which the PNAs are attached is typically glass, quartz, or nylon membranes. It is also possible to employ a gold or platinum film over some solid support and attach the PNAs to that using chemistries developed by Whitesides and disclosed in C. D. Bain, E. B. Troughton, Y-T Tao, J. Evall, G. M. Whitesides, and R. G. Nuzzo, *J. Am. Chem. Soc.* 111, 321 (1989). The attachment of the PNA can occur after the synthesis of the PNA sequence that contains a terminal amine residue. Using silicon chemistry, as disclosed in Z. Guo, R. A. Guilfoyle, A. J. Thiel, R. Wang, L. M. Smith, *Nucleic Acids Research* 22, 5456, (1994), linkers can be made to attach to a $SiO_2$ surface or glass surface and provide a reactive site for the terminal amine on the PNA. Alternatively the PNAs could be synthesized in situ on the surface of the chip as described by Fodor et al. in S.P.A. Fodor, J. L. Read, M. C. Pirrung, L. Stryer, A. T. Lu, D. Solas, *Science* 251, 767 (1991). FIG. 1 shows the results of SIRIS analysis of a Format II SBH chip in which the attached PNA was hybridized with DNA. The DNA is observed, by phosphorous detection, at the location of complementary hybridization. Phosphorous is not detected at the location of the non-complementary PNA, thus distinguishing between complementary and non-complementary sequences.

Format I SBH requires that the DNA be attached to the genosensor surface. This is done by using methods similar to those currently used for Format I SBH using labeled ODNs for detection as noted in R. Drmanac, S. Drmanac, I. Labat, R. Crkvenjakov, A. Vicentic, and A. Gemmell, *Electrophoresis* 13, 566–573 (1992).

Hybridization of test DNA to the sequence-specific PNAs on the surface is carried out in Format II SBH and hybridization of the sequence-specific PNAs to the DNA on the surface would be performed for Format I SBH. The sequence of the test DNA is determined by scanning the genosensor chip with a position sensitive detector to detect the presence (Format II) or reduction (Format I) of phosphorus, phosphorus compounds, and/or organic substances unique to normal DNA at or near the surface of the genosensor chip.

A nonoptimal resonance ionization spectroscopy (RIS) scheme has been used to detect phosphorus in adenosine-5'-phosphate. In this analysis, a series of 5 µl samples of different concentrations of adenosine-5'-phosphate were deposited and dried onto a silicon surface. Data obtained from this analysis revealed that the phosphorus signal was strong and that the strength of the signal was a function of the amount of the sample. Stronger signals are obtained when the RIS process is optimized or when negative ion Secondary Ion Mass Spectrometry (SIMS) or Laser Ionization Mass Spectrometry (LIMS) is utilized.

The sensitivity of these detection schemes is such that as few as 100–10,000 atoms can be detected, depending on the characteristics of the element. In the case of phosphorus or phosphorus oxide molecules, the higher detection level would apply, which corresponds to ~$10^{-19}$ mole, a level that is comparable to the amounts of radioisotope or fluorescent labels used in other procedures. The novel aspect of this invention is that no extrinsic label is required since the phosphorus of the test DNA is used to detect its presence on the PNA site on the chip. Furthermore, each base in single stranded DNA contains one phosphorous atom and therefore, a five hundred base fragment will contain five hundred phosphorous atoms available for detection.

The main requirements for the detection technique are that it be very sensitive, have good spatial resolution, and be capable of distinguishing the unique components of DNA, such as phosphorus or deoxyribose derivatives. Several mass spectrometric techniques fall into this category; these include SIRIS, LARIS, secondary ion mass spectrometer (SIMS), laser ionization mass spectrometry (LIMS, also known as laser microprobe mass analysis or LAMMA), and nonresonant or sub-nanosecond post-ionization techniques. Among the non-mass spectrometric methods that are also suitable are: atomic force microscopy, reflectance spectroscopy, second harmonic generation on surfaces, polarization techniques such as ellipsometry, Raman spectroscopy, and surface enhanced Raman spectroscopy.

BRIEF DESCRIPTION OF THE DRAWINGS

FIG. 1A. FIG. 1A shows a diagram of an SBH chip on which two different PNA oligos that were attached in separate locations. Position A=PNA oligo which is complementary to the M13(-20) DNA oligonucleotide probe and position B=PNA oligo which is not complementary to the M13(-20) DNA oligonucleotide probe. The DNA chip was hybridized with the M13(-20) DNA oligonucleotide.

FIG. 1B. FIG. 1B displays a SIRIS (sputter-initiated resonance ionization spectroscopy) image of the phosphorus detected on the surface of the SBH chip. Phosphorous is observed where the DNA nucleotide is located, demonstrating successful detection of hybridization of DNA to PNA.

BEST MODE FOR CARRYING OUT THE INVENTION

PNA oligomers are synthesized like DNA oligomers in that the synthesis begins with the four different monomers and links them together to form the oligomer of desired sequence. In the case of PNA, the monomers for making PNA each contain one of the four bases (adenine, guanine, thymine, or cytosine) attached to 2-aminoethyl glycine. PNA monomers have amino and carboxyl termini, which are similar to amino acids. PNA monomers are linked by peptide bonds to form an oligomer and the synthesis protocols required to link the monomers are the same as those used for standard peptide synthesis. Therefore, the PNA oligomers can be synthesized on a resin and then cleaved from that resin and applied to the SBH surface. Alternatively, they can be synthesized directly on the SBH chip as is currently being done with DNA oligomers, using photolithography, physical masking, or ink jet application techniques.

Using the polymerase chain reaction (PCR), defined strands of double-stranded DNA can be replicated for hybridization to the set of known-sequence PNAs in the SBH Format II process. After hybridization of the DNA to the PNA, DNA will be attached only at sites containing complementary PNA sequences. The genosensor chip can be inserted into a vacuum chamber for Laser Ionization Mass Spectrometry (LIMS) analysis of the PNA sites. In the LIMS analysis, a laser is used to desorb a small amount of material from the PNA sites. A small fraction of this material will be ionized and the resulting ions can be mass analyzed by a mass spectrometer. In particular, the negative phosphates ions and negative ions of other phosphorus compounds will indicate that DNA is present and therefore hybridization has occurred.

LIMS may be employed to scan a SBH chip mounted on a support by moving the support while the laser beam position remains fixed. Alternatively, the sample can remain fixed in position and the surface scanned rapidly with the laser beam. The laser beam can be focused to <10 $\mu$m in diameter to improve the resolution between adjacent DNA positions of the chip. It is also possible to use a large spot size laser beam to simultaneously desorb sample from many or all of the hybridization positions on the chip, and image the resulting ions on the detector.

Those skilled in the art will recognize that the signal from surface analysis techniques such as LIMS or other surface analysis techniques such as those methods described below will indicate the reduction in surface concentration of constituents of the target material (for example, DNA) when it is covered by a different material (for example, PNA) that does not contain those constituents. In this way, the above technique is adaptable for use in Format I SBH where DNA is attached to a surface and PNA is hybridized to the immobilized DNA.

Those skilled in the art will also recognize that the small number of ions produced in the LIMS process can be enhanced by nonresonant laser ionization (surface analysis by laser ionization, SALI) or resonance laser ionization (LARIS).

Those skilled in the art will further recognize that the ablation laser in LIMS can be replaced by an ion beam, as in SIMS, sputtered neutral mass spectrometry (SNMS), or SIRIS.

Moreover, those skilled in the art will recognize that several non-mass spectrometry techniques, such as second harmonic generation on surfaces, Raman, surface enhanced Raman, ellipsometry, and reflectance spectrometry can also be used to monitor the surface composition.

Those skilled in the art will readily recognize that the present invention could also be practiced for determining RNA sequences. One skilled in the art could obtain DNA by reverse transcription of RNA from the source of interest.

Data from the LIMS analysis can be displayed digitally or in graphic form that is comparable to images obtained from autoradiography or fluorescent analyses. The sequence obtained could be printed out directly and any uncertainties designated. Relative to radiation safety, the purchase and disposal of radioisotopes is eliminated and the process is safer for personnel.

From the foregoing description, it will be recognized by those skilled in the art that the present DNA sequencing, mapping, and diagnostic processes, which utilizes hybridization and unlabeled DNA, offer several distinct advantages over the prior art. Specifically, the DNA Sequencing, Mapping, and Diagnostic Processes Using Hybridization Chips and Unlabeled DNA provides costs savings by eliminating the time and chemicals needed by other techniques to label the DNA or substance hybridized to the DNA (ODNs or PNAs).

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention,

We claim:

1. A method for analyzing hybridized nucleic acids, said method comprising the steps of:

attaching PNA segments of known sequence to a hybridization surface;

causing DNA fragments to hybridize to said PNA segments fixed on said hybridization surface;

rinsing non-hybridized DNA fragments from said hybridization surface; and detecting the hybridized DNA fragments on said hybridization surface by detection of elements or compounds which are exclusive to DNA as compared to PNA.

2. The method of claim 1 wherein said hybridization surface is composed of a chemical material selected from the group consisting of glass, Pyrex®, silicon, silicon oxide, nylon membranes, polypropylene, gold surfaces, and platinum surfaces.

3. The method of claim 2 wherein said PNA segments attached to said hybridization surface contain sequences that distinguish normal from abnormal DNA sequences in a subject gene, thereby enabling detection of mutations in DNA.

4. The method of claim 1 wherein said hybridized DNA fragments on said hybridization surface are detected by mass spectrometry techniques selected from the group consisting of time-of-flight, quadrupole, magnetic sector and ion trap mass spectrometry.

5. The method of claim 1 further comprising the step of analyzing said hybridized DNA fragments detected on said hybridization surface using a surface analysis technique, said surface analysis technique including at least the step of vaporizing said hybridized DNA fragments.

6. The method claim 5 wherein said surface analysis technique further includes the step of ionizing said vaporized, hybridized DNA fragments.

7. The method of claim 6 wherein said surface analysis technique steps of vaporizing and ionizing said hybridized DNA fragments are accomplished simultaneously.

8. The method of claim 7 wherein said surface analysis technique is selected from the group consisting of secondary ion mass spectroscopy (SIMS), laser ionization mass spectroscopy (LIMS), and laser microprobe mass analysis (LAMMA).

9. The method of claim 6 wherein said step of ionizing said vaporized, hybridized DNA fragments is accomplished using a resonance ionization method.

10. The method of claim 9 wherein said step of vaporizing said hybridized DNA fragments which are analyzed using a resonance ionization method is performed by a technique selected from the group consisting of ion beam sputtering, sputter-initiated resonance ionization spectroscopy (SIIUS) using at least one resonance laser, laser ablation, laser desorption, laser atomization resonance ionization spectroscopy (LARIS) using at least one resonance laser, and a thermal technique.

11. The method of claim 10 wherein said at least one laser is selected from the group consisting of a wavelength tunable laser and a fixed-wavelength laser that has a coincidental overlap between their wavelength and an electronic transition in the element to be analyzed.

12. The method of claim 11 wherein said wavelength tunable laser is selected from the group consisting of a diode laser, a dye laser, an optical parametric oscillator, and a solid-state laser.

13. The method of claim 11 wherein said fixed-wavelength laser is selected from the group consisting of a gas laser and a solid-state laser.

14. The method of claim 6 wherein said step of ionizing said vaporized, hybridized DNA fragments is accomplished using a nonresonance ionization method.

15. The method of claim 14 wherein said step of vaporizing said hybridized DNA fragments which are analyzed using a nonresonant ionization method is performed by a technique selected from the group consisting of ion beam sputtering, laser ablation, laser-induced desorption, and a thermal technique.

16. The method of claim 15 wherein said nonresonant ionization is performed using a method selected from the group consisting of a continuous wave laser, a pulsed laser, electron collision, and plasma.

17. The method of claim 16 wherein said pulsed laser is selected from the group consisting of an excimer, a Nd:YAG (Neodinium: Yttrium Aluminum Garnet), a Cu-vapor, and a sub-nanosecond laser.

18. The method of claim 5 wherein said surface analysis technique further includes the step of analyzing said vaporized, hybridized DNA fragments by a technique which does not require ionization.

19. The method of claim 18 wherein said surface analysis technique is accomplished using at least one nonionization technique selected from the group consisting of resonant and nonresonant Raman spectroscopy, resonant fluorescence spectroscopy, nonresonant fluorescence spectroscopy, absorption spectroscopy, optical emission of laser ablated material, and optical emission of ion beam sputtered material.

20. The method of claim 1 further comprising the step of analyzing said hybridized DNA fragments detected on said hybridization surface using a surface analysis technique which does not require vaporization.

21. The method of claim 20 wherein said surface analysis technique which does not require vaporization is selected from the group consisting of Raman spectroscopy, surface-enhanced Raman spectroscopy (SERS), second-harmonic generation (SHG), Auger electron spectroscopy, x-ray photon spectroscopy, ellipsometry, and fluorescence spectroscopy.

22. A method for analyzing hybridized nucleic acids, said method comprising the steps of:

attaching DNA fragments to a hybridization surface;

causing PNA segments of known sequence to hybridize to said DNA fragments fixed on said hybridization surface;

rinsing nonhybridized PNA segments from said hybridization surface; and detecting hybridized PNA segments on said hybridization surface by detection of a reduction in surface concentration of elements or compounds which are exclusive to DNA as compared to PNA.

23. The method of claim 22 wherein said hybridization surface is composed of a chemical material selected from the group of chemical materials consisting of glass, Pyrex®, silicon oxide, nylon membranes, polypropylene, gold surfaces, and platinum surfaces.

24. The method of claim 23 wherein said PNA segments attached to said hybridization surface contain sequences that distinguish normal from abnormal DNA sequences in a subject gene, thereby enabling detection of mutations in DNA.

25. The method of claim 22 wherein said hybridized PNA segments on said hybridization surface are detected by mass spectrometry techniques selected from the group consisting of time-of-flight, quadrupole, magnetic sector and ion trap mass spectrometry.

26. The method of claim 22 further comprising the step of analyzing said labeled hybridized DNA fragments detected on said hybridization surface using a surface analysis technique, said surface analysis technique including at least the step of vaporizing said hybridized DNA fragments.

27. The method of claim 26 wherein said surface analysis technique further includes the step of ionizing said vaporized, hybridized DNA fragments.

28. The method of claim 27 wherein said surface analysis technique steps of vaporizing and ionizing said hybridized DNA fragments are accomplished simultaneously.

29. The method of claim 28 wherein said surface analysis technique is selected from the group consisting of secondary ion mass spectroscopy (SIMS), laser ionization mass spectroscopy (LIMS), and laser microprobe mass analysis (LAMMA).

30. The method of claim 27 wherein said step of ionizing said vaporized, hybridized DNA fragments is accomplished using a resonance ionization method.

31. The method of claim 30 wherein said step of vaporizing said hybridized DNA fragments which are analyzed using a resonance ionization method is performed by a technique selected from the group consisting of ion beam sputtering, sputter-initiated resonance ionization spectroscopy (SIRIS) using at least one resonance laser, laser ablation, laser desorption, laser atomization resonance ionization spectroscopy (LARIS) using at least one resonance laser, and a thermal technique.

32. The method of claim 31 wherein said at least one laser is selected from the group consisting of a wavelength tunable laser or a fixed-wavelength laser that have a coincidental overlap between their wavelength and an electronic transition in the element to be analyzed.

33. The method of claim 32 wherein said wavelength tunable laser is selected from the group consisting of a diode laser, a dye laser, an optical parametric oscillator, and a solid-state laser.

34. The method of claim 32 wherein said fixed-wavelength laser is selected from the group consisting of a gas laser and a solid-state laser.

35. The method of claim 27 wherein said step of ionizing said vaporized, hybridized DNA fragments is accomplished using a nonresonance photoionization method.

36. The method of claim 35 wherein said step of vaporizing said hybridized DNA fragments which are analyzed using a nonresonant ionization method is performed by a technique selected from the group consisting of ion beam sputtering, laser ablation, laser-induced desorption, and a thermal technique.

37. The method of claim 36 wherein said nonresonant ionization is performed using a method selected from the group consisting of a continuous wave laser, a pulsed laser, electron collision, and plasma.

38. The method of claim 37 wherein said pulsed laser is selected from the group consisting of an excimer, a Nd:YAG (Neodinium:Yttrium Aluminum Garnet), a Cu-vapor, and a sub-nanosecond laser.

39. The method of claim 26 wherein said surface analysis technique further includes the step of analyzing said vaporized, hybridized DNA fragments by a technique which does not require ionization.

40. The method of claim 39 wherein said surface analysis technique is accomplished using at least one nonionization technique selected from the group of techniques consisting of resonant Raman spectroscopy, nonresonant Raman spectroscopy, resonant fluorescence spectroscopy, nonresonant fluorescence spectroscopy, absorption spectroscopy, optical emission of laser ablated material and optical emission of ion beam sputtered material.

41. The method of claim 22 further comprising the step of analyzing said hybridized DNA fragments detected on said hybridization surface by a surface analysis technique which does not require vaporization.

42. The method of claim 41 wherein said surface analysis technique which does not require vaporization is selected from the group of techniques consisting of Raman spectroscopy, surface-enhanced Raman spectroscopy (SERS), second-harmonic generation (SHG), Auger electron spectroscopy, x-ray photon spectroscopy, ellipsometry, and fluorescence spectroscopy.

* * * * *